United States Patent [19]
Cullen

[11] 3,993,681
[45] Nov. 23, 1976

[54] PROCESS FOR PREPARING IMINODIACETONITRILE

[75] Inventor: Barry Allen Cullen, Nashua, N.H.

[73] Assignee: W. R. Grace & Co., New York, N.Y.

[22] Filed: Jan. 26, 1976

[21] Appl. No.: 652,497

Related U.S. Application Data

[63] Continuation-in-part of Ser. No. 565,148, April 4, 1975, abandoned.

[52] U.S. Cl. .................. 260/465.5 A; 260/465.5 R
[51] Int. Cl.² ........................................ C07C 120/00
[58] Field of Search .............. 260/465.5 A, 465.5 R

[56] References Cited
UNITED STATES PATENTS

| | | | |
|---|---|---|---|
| 2,511,487 | 6/1950 | Thompson | 260/465.5 A |
| 2,794,044 | 5/1957 | Miller | 260/465.5 A |
| 3,167,580 | 1/1965 | Saunders et al. | 260/465.5 A |
| 3,412,137 | 11/1968 | Stutts | 260/465.5 A |

FOREIGN PATENTS OR APPLICATIONS

| | | | |
|---|---|---|---|
| 684,850 | 4/1964 | Canada | 260/465.5 A |

*Primary Examiner*—Joseph Paul Brust
*Attorney, Agent, or Firm*—Elton Fisher

[57] ABSTRACT

Iminodiacetonitrile is prepared by a batch process comprising reacting hexamethylenetetramine and HCN in an aqueous medium in the presence of a strong acid at a pH of 5.5–6.5 while maintaining an excess of HCN in the reaction mixture.

7 Claims, No Drawings

PROCESS FOR PREPARING IMINODIACETONITRILE

CROSS-REFERENCE TO RELATED APPLICATION

This is a continuation-in-part of our copending application, Ser. No. 565,148, filed Apr. 4, 1975, and now abandoned.

BACKGROUND OF THE INVENTION

This invention relates to iminodiacetonitrile (IDAN). More specifically this invention is directed to an improved process for preparing IDAN.

Eschweiler described a method (Ann. 1894, 278, 229–239) wherein IDAN is formed by the reaction of hexamethylenetetramine (HMTA) and HCN in an aqueous medium.

Other methods for preparing IDAN are taught by U.S. Pat. No. 3,167,580 (Saunders et al, 260/465.5), U.S. Pat. No. 3,412,137 (Stutts, 260/465.5), U.S. Pat. No. 2,794,044 (Miller, 260/465.5), U.S. Pat. No. 2,511,487 (Thompson, 260/465), and Canadian Pat. No. 684,850 (Koenig).

Saunders et al, and Miller replaced the HMTA of Eschweiler with formaldehyde and ammonia while Stutts used Eschweiler's reactants (HMTA and HCN) in aqueous acetic acid.

Thompson prepares IDAN by reacting aminoacetonitrile (glycinonitrile) with formaldehyde cyanohydrin (glycolonitrile) in the presence of a mineral acid stabilizer.

Koenig prepared IDAN by: (a) reacting HMTA or the amounts of formaldehyde and ammonia required for the formation thereof with HCN in the presence of a solvent (e.g., water); and (b) subsequently acidifying the reaction mixture with a strong mineral acid.

SUMMARY OF THE INVENTION

In summary, this invention is directed to an improvement in a process for preparing iminodiacetonitrile comprising reacting hexamethylenetetramine and HCN in an acidic aqueous medium and recovering the iminodiacetonitrile, the improvement comprising:

a. forming a first solution by admixing anhydrous HCN and a second solution having a pH of 5–7, a temperature of 0°–50° C, and consisting essentially of water, a strong acid, and hexamethylenetetramine, the HCN present in the first solution being 6–50% of that used per batch and the hexamethylenetetramine present in the first solution being 0.5–45% of that used per batch, the mole ratio of HCN to hexamethylenetetramine in the first solution being greater than 6:1 and less than 12:1;

b. forming a third solution by simultaneously adding to the first solution: (i) anhydrous HCN; and (ii) a fourth solution consisting essentially of water, hexamethylenetetramine, and the strong acid while maintaining a temperature of the resulting third solution at 10°–75° C, the fourth solution containing one mole of hexamethylenetetramine per equivalent of the acid, the anhydrous HCN and the fourth solution being added at rates such that: (I) the mole ratio of HCN to hexamethylenetetramine in the third solution is at least 6:1; and (II) the pH of the third solution is 5.5–6.5;

c. adjusting the temperature of the third solution to 30°–70° C if it is not already within this temperature range; and d. forming iminodiacetonitrile by adding to the third solution over a period of time effective for forming iminodiacetonitrile an amount of the strong acid effective for maintaining the pH of the resulting mixture at 5.5–6.5 while maintaining the temperature thereof at 30°–70° C.

DESCRIPTION OF PREFERRED EMBODIMENTS

In preferred embodiments of the invention set forth in the above summary:

1. The temperature of the first solution is maintained at 10°–65° C.
2. The temperature of the third solution is maintained at 30°–70° C.
3. The strong acid is sulfuric acid.
4. The HCN and the second solution are admixed to form the first solution while maintaining the temperature of the resulting first solution at 25°–65° C.
5. The HCN and the second solution are admixed at rates to provide 6.5–8 moles of HCN per mole of hexamethylenetetramine in the resulting first solution.
6. The mole ratio of HCN to hexamethylenetetramine in the third solution is maintained within the range of 6.1–7:1.

Because of my disclosure it will be readily apparent to those skilled in the art that cooling (e.g., with internal or external cooling coils, with a cooling jacket, a cooling bath, or the like) can be used to cool reacting materials and/or reaction products. Likewise, if necessary (e.g., where working in very cold areas), heating coils or jackets or baths, or electric heating apparatus, or the like can be used to provide heat to reacting mixtures and reaction products.

DETAILED DESCRIPTION OF THE INVENTION

The following equation shows the stoichiometry of the formation of IDAN from HMTA in the presence of sulfuric acid (other strong acid can be substituted for $H_2SO_4$):

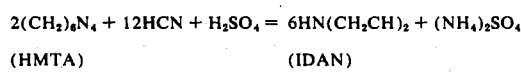

$$2(CH_2)_6N_4 + 12HCN + H_2SO_4 = 6HN(CH_2CH)_2 + (NH_4)_2SO_4$$
(HMTA) (IDAN)

I have found that where using the four-step improvement recited in the above Summary the yield of IDAN (based on HMTA charged) is about 4% better than that of the prior art and reaction time is about one-half that of the prior art. The IDAN obtained using said improvement is pure IDAN (i.e., IDAN which is free of impurities and side products such as other aminoacetonitriles including nitrilotriacetonitrile (NTAN) and substantially free of color bodies). The presence of NTAN in IDAN is especially objectionable because when the IDAN is converted to IDA (iminodiacetic acid) the NTAN contaminant is converted to NTA (nitrilotriacetic acid) which is substantially less soluble in water than IDA.

While I generally prefer to use a strong mineral acid such as sulfuric acid, hydrochloric acid, pyrophosphoric acid, and the like in the process of this invention, strong organic acids can also be used in the process of said invention. For ecomonic reasons sulfuric acid is the preferred strong acid.

The IDAN product is generally separated (e.g., by decantation, filtration, or centrifugation) from the mother liquor in which it is formed and recovered as IDAN. However, if desired, the IDAN can be saponified ((hydrolyzed) with caustic alkali (e.g., NaOH or KOH) to form dialkali metal iminodiacetate, by-product ammonia and a by-product alkali metal salt of the strong acid. The by-product ammonia can be evaporated from the system and recovered.

Where the strong acid is sulfuric acid and the caustic alkali is sodium hydroxide, the dialkali metal iminodiacetate is disodium iminodiacetate and the by-product alkali metal salt of the strong acid is sodium sulfate. In this instance, the disodium iminodiacetate can be converted to iminodiacetic acid (IDA) by treatment with sulfuric acid and the sodium sulfate and IDA can be separated by the method of U.S. Pat. No. 3,808,269.

Where the strong acid is hydrochloric acid and the caustic alkali is sodium hydroxide, the dialkali metal iminodiacetate is disodium iminodiacetate and the by-product alkali metal salt of the strong acid is sodium chloride. In this instance, the disodium iminodiacetate can be converted to iminodiacetic acid (IDA) by treating the disodium iminodiacetate with hydrochloric acid and the sodium chloride and IDA can be separated by the method of U.S. Pat. No. 3,852,344.

Because of my disclosure other procedures for separating and recovering IDAN and IDA will be readily apparent to those skilled in the art.

The process of this invention can be conducted in a vented reactor or in a closed reactor.

The instant invention will be better understood by referring to the following specific but nonlimiting example and procedures. It is understood that said invention is not limited by this example and the procedures which are offered merely to illustrate the invention; it is also understood that modifications can be made without departing from the spirit and scope of the invention.

The example was actually run.

The procedures, while not actually run, will illustrate certain embodiments of my invention.

EXAMPLE

A second aqueous solution having a pH of 5.5 was prepared in a reaction zone (a 1 liter round bottom flask) vented to the atmosphere via a reflux condenser and provided with a mechanical stirrer, a pH probe (an electrode for use in determining the pH of material in the reaction zone), and three addition ports (addition funnels) by adding thereto a 47.2 g portion of a 30% solution of HMTA in water (0.1mole HMTA), said HMTA solution having a temperature of about 25° C, and 2.5 g of an aqueous 98% sulfuric acid solution (0.025 mole of $H_2SO_4$) having a temperature of about 25° C while stirring the HMTA solution and the resulting second aqueous solution. The temperature of the second aqueous solution was adjusted to 25° C.

A first aqueous solution having a pH of 6 and a temperature of about 60° C was prepared by adding 20 g (0.74 mole) of liquid anhydrous HCN to the second aqueous solution in said vented reaction zone while stirring the material in said reaction zone. The temperature of the material in said reaction zone increased rapidly to 62° C when the HCN was added. An external cooling bath was applied to said reaction zone (the 1 liter flask) to cool the first aqueous solution to about 60° C.

A third aqueous solution having a pH of 6 and a temperature of 40° C was formed by concurrently feeding into the first aqueous mixture in said reaction zone (while stirring and cooling the material in said reaction zone); (a) 424.8 g of a fourth aqueous solution consisting essentially of water, HMTA, and sulfuric acid, the fourth aqueous solution analyzing 30% HMTA and having a pH of 4.6 and a temperature of about 25° C; and (b) 144 g (5.33 mole) of liquid anhydrous HCN having a temperature of about 25° C while maintaining the temperature of the material in said reaction zone at about 40° C. Feed time was 45 minutes. The fourth aqueous solution and the liquid anhydrous HCN were added to said reaction zone at such rates that an excess of HCN over that required by the stoichiometry was continuously maintained in said reaction zone.

IDAN was prepared by adding (over a period of about an hour) to the third aqueous solution in said reaction zone (while stirring the material in the reaction zone and while maintaining the temperature thereof at about 50°–60° C) 13 g of an aqueous 98% sulfuric acid solution (0.13 mole $H_2SO_4$) to maintain the pH of the material in said reaction zone at 6. After adding the sulfuric acid solution, the material in said reaction zone was cooled to 25° C and the precipitated IDA was separated by centrifugation, washed with cold (ca. 15° C) water, air dried and recovered. The recovered IDAN product weighed 250.8 g and analyzed 95.6% IDAN and 4% moisture representing a conversion (one pass yield) of 84% based on the HMTA charged.

PROCEDURE 1

The general method of Example 1 can be repeated in a modified form wherein 12 molar hydrochloric acid (aqueous HCl) is used in place of sulfuric acid to maintain and adjust the pH. The results of such run will be indistinguishable from those in Example 1.

PROCEDURE 2

Other runs can be made using the general method of Example 1 in which the 98% $H_2SO_4$ used to adjust and maintain the pH in Example 1 is replaced with; (a) an aqueous 50% $H_2SO_4$ solution; (b) an aqueous 25% $H_2SO_4$ solution; (c) 6 molar hydrochloric acid; (d) 6 molar nitric acid ($HNO_3$ in water); (e) pyrophosphoric acid; or (f) other strong acid. In each instance the results will be substantially indistinguishable from those obtained in Example 1.

PROCEDURE 3

Another run can be made using the general method of Example 1 wherein said method is modified by adding a second aqueous solution containing 0.1 mole of HMTA and 0.025 mole of $H_2SO_4$ to an aqueous solution of 0.8 mole of HCN in a reaction zone to form the first aqueous solution. The results of such run will be substantially identical with those of Example 1.

PROCEDURE 4

Another series of 5 runs can be made wherein the method of Example 1 is modified by varying the mole ratio of HCN to HMTA in the third solution of the above Summary from run to run as follows:

| Run No. | Mole Ratio, HCN:HMTA In the Third Solution of the Above Summary |
|---|---|
| 1 | 6.1–6.2:1 |
| 2 | 6.3–6.4:1 |
| 3 | 6.6–6.8:1 |
| 4 | 6.9–7:1 |

-continued

| Run No. | Mole Ratio, HCN:HMTA In the Third Solution of the Above Summary |
|---|---|
| 5 | 7.8-8:1 |

The results of said runs (Runs 1–5) will be substantially identical with those obtained in Example 1.

PROCEDURE 5

The general method of Example 1 can be repeated in a modified form wherein trifluoroacetic acid (a strong organic acid) is substituted for sulfuric acid. The results of such run will be substantially the same as those of Example 1.

While the exact temperature of the liquid anhydrous HCN used as feed in the process of my invention is not critical, I generally prefer for it (the HCN) to have a temperature of about 0°–25° C. However higher temperatures and lower temperatures have given excellent results. Excellent results can be obtained with anhydrous HCN fed as vapor (which is fully equivalent to liquid anhydrous HCN). However I generally prefer to use liquid anhydrous HCN as a feedstock for the process of this invention.

The exact temperatures of $H_2SO_4$ (or other strong acid) and aqueous HMTA plus acid (the second aqueous solution of the above Summary) are not critical, but I generally prefer for these to have temperatures of about 15°–25° C to reduce the amount of external cooling required (and to permit faster feed rates). However excellent results can be obtained with temperatures below 15° C and above 25° C.

Residence times in the reactor in which the IDAN is formed is not critical, but it is, in each instance, important that residence time be for a period effective for a substantial portion of the reactants to react.

IDAN is an intermediate on a route to iminodiacetic acid (IDA) which can be prepared from IDAN by a method taught by Eschweiler (Ann. 1894, 278, 299–239). IDA is used in metal plating baths. German Pat. No. 1,034,946 (Chem. Abstracts 1960, 54, 16237e) teaches the use of IDA in cyanide-containing copper (and copper alloy) plating baths. The presence of IDA in such baths causes copper (or the copper alloy) to plate (precipitate) as a bright coating.

The use of IDA in the preservation of rubber latex is taught by British Pat. No. 800,089 (Chem. Abstracts 1959, 53, 2672i).

When heated in an aqueous medium with about a stoichiometric quantity sodium hydroxide solution IDAN yields disodium iminodiacetate ($IDANa_2$) according to the following equation:

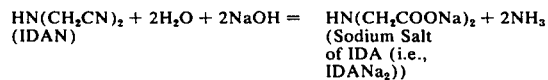

French Pat. No. 1,190,714 (Chem. Abstracts 1960, 54, 25993g) teaches the use of $IDANa_2$ as an agent for removing residual catalyst (e.g., Ti, Cr, Fe, V, or Al salts) from polyolefins.

As used herein the term percent (%) means parts per hundred and parts means parts by weight unless otherwise defined where used.

As used herein the term mole has its generally accepted meaning, i.e., a mole of a substance is that quantity which contains the same number of molecules of the substance as there are atoms in 12 grams of pure $^{12}C$.

As used herein the term "g" means gram or grams.
IDA means iminodiacetic acid.
IDAN means iminodiacetonitrile.
$IDANa_2$ means disodium iminodiacetate.
NTA means nitrilotriacetic acid.
$NTANa_3$ means trisodium nitrilotriacetate.
NTAN means nitrilotriacetonitrile.
HMTA means hexamethylenetetramine.

As is well known to those skilled in the art, a strong acid is an acid having at least one ionization constant ($K_a$) within a range of about $10^{-2}$ to $10^{-1}$ or greater, (e.g., $10^{-2}$ to $10^0$). I generally prefer to use strong mineral acids although, as noted supra, strong organic acids are operable. However, for the purpose of this invention, any strong acid is equivalent to sulfuric acid which, because of economic and accounting reasons, is a preferred strong acid.

I claim:
1. In a batch process for preparing iminodiacetonitrile comprising reacting hexamethylenetetramine and HCN in an acidic aqueous medium and recovering the iminodiacetonitrile, the improvement comprising:
   a. forming a first solution by admixing anhydrous HCN and a second solution having a pH of 5–7, a temperature of 0°–50° C, and consisting essentially of water, a strong acid, and hexamethylenetetramine, the HCN present in the first solution being 6–50% of that used per batch and the hexamethylenetetramine present in the first solution being 0.5–45% of that used per batch, the mole ratio of HCN to hexamethylenetetramine in the first solution being greater than 6:1 and less than 12:1;
   b. forming a third solution by simultaneously adding to the first solution: (i) anhydrous HCN; and (ii) a fourth solution consisting essentially of water, hexamethylenetetramine, and the strong acid while maintaining the temperature of the resulting third solution at 10°–75° C, the fourth solution containing one mole of hexamethylenetetramine per equivalent of the acid, the anhydrous HCN and the fourth solution being added at rates such that: (I) the mole ratio of HCN to hexamethylenetetramine in the third solution is at least 6:1; and (II) the pH of the third solution is 5.5–6.5;
   c. adjusting the temperature of the third solution to 30°–70° C if it is not already within this temperature range; and
   d. forming iminodiacetonitrile by adding to the third solution over a period of time effective for forming iminodiacetonitrile an amount of the strong acid effective for maintaining the pH of the resulting mixture at 5.5–6.5 while maintaining the temperature thereof at 30°–70° C.

2. The process of claim 1 in which the temperature of the first solution is maintained at 10°–65° C.

3. The process of claim 1 in which the temperature of the third solution is maintained at 30°–70° C.

4. The process of claim 1 in which the strong acid is sulfuric acid.

5. The process of claim 1 in which HCN and the second solution are admixed to form the first solution while maintaining the temperature of the resulting first solution at 25°–65° C.

6. The process of claim 1 in which HCN and the second solution are admixed at rates to provide 6.5–8 moles of HCN per mole of hexamethylenetetramine in the resulting first solution.

7. The process of claim 1 in which the mole ratio of HCN to hexamethylenetetramine in the third solution is maintained within the range of 6.1–7:1.

* * * * *